United States Patent [19]

Piotrowski et al.

[11] Patent Number: 4,788,368

[45] Date of Patent: Nov. 29, 1988

[54] SYNTHESIS OF OLEFINS FROM KETONES USING A BIS(SUBSTITUTED ALUMINO) SUBSTITUTED METHANE

[75] Inventors: Andrzej M. Piotrowski, Houston; Dennis B. Malpass, La Porte, both of Tex.; John J. Eisch, Vestal; Marek P. Boleslawski, Binghamton, both of N.Y.

[73] Assignee: Texas Alkyls Inc., Deer park, Tex.

[21] Appl. No.: 116,845

[22] Filed: Nov. 5, 1987

[51] Int. Cl.$^4$ .............................................. C07C 1/20
[52] U.S. Cl. .................................. 585/357; 585/469; 585/638
[58] Field of Search ....................... 585/357, 469, 638

[56] References Cited

PUBLICATIONS

J. of Organometallic Chem., 72(1974) C4–C6.
J. of Organometallic Chem., 225 (1982) 71–85.
Tetrahedron Letters No. 48, pp. 6021–6025, 1966.

*Primary Examiner*—Curtis R. Davis
*Attorney, Agent, or Firm*—Richard P. Fennelly; Louis A. Morris

[57] ABSTRACT

Ketones are alkylenated to form the corresponding olefin by reaction with a bis(substituted alumino)substituted methane, e.g., in the form of its dietherate.

7 Claims, No Drawings

SYNTHESIS OF OLEFINS FROM KETONES USING A BIS(SUBSTITUTED ALUMINO) SUBSTITUTED METHANE

BACKGROUND OF THE INVENTION

1. Field of the Invention

The present invention relates to the synthesis of olefins from ketones using a bis(substituted alumino)substituted methane compound as an organoaluminum alkylenating agent whereby the carbonyl oxygen atom of the ketone is replaced with an alkylene group to form the corresponding olefin.

2. Description of the Prior Art

Conversion of a carbonyl function to a carbon-carbon double bond is a known industrial procedure. It is commonly achieved by use of phosphorus ylids in the Wittig reaction. Although such a reaction is general for both aldehydes and ketones, in certain instances poor yields of olefinic products are obtained when carbonyl compounds are attacked by the highly reactive bases used to generate phosphorus ylids. In view of the market potential for the reaction and certain disadvantages in regard to use of Wittig reagents, some other alternatives have been examined.

Gem-dimetallic derivatives, such as bishalomagnesiomethane, have been proposed for use (F. Bertini et al., Tetrahedron 26, 1281, 1970) but such geminal dimagnesium compounds are difficult to make and are thus expensive.

Geminal dialuminum compounds, such as bisdibromoaluminomethane, are more inexpensive to prepare but were found by A. Bongini et al. (J. of Organomet, Chem., 72 (19474) C4–C6) to be quite unreactive towards ketones.

Ashby et al. (J. of Organomet. Chem., 225 (1982) 71–85) utilized bis(diethylalumino)methane to ethylate 4-t-butylcyclohexanone. Ashby et al. observed 4-t-butyl-1-methylenecyclohexane in the product, but the relatively low yield (43%) would not justify use of bis(diethylalumino)methane as a Wittig reagent replacement.

3. Related Application

In copening U.S. Ser. No. 116,846, filed on even date herewith, the synthesis of olefins from ketones using bis(alkylchloroalumino)methane as a methylenating agent is described.

SUMMARY OF THE INVENTION

The present invention relates to the use of bis(substituted alumino)substituted methane reagents to convert ketones to olefins. Good yields (e.g., 50–80%) of olefins from ketones was achieved by using compounds containing alkyl, halo or mixed haloalkyl substitution on aluminum and a pentyl-substituted methylene bridging group between the two aluminum atoms in the alkylenating reagent as the substituted methane moiety.

DETAILED DESCRIPTION OF THE INVENTION

The bis(substituted alumino)substituted methane reagents intended for use in accordance with the present invention have the formula:

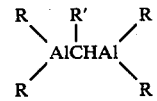

where R is hydrocarbyl, such as alkyl (e.g., $C_1$–$C_4$ alkyl, such as methyl or ethyl), halo (e.g., chloro), or mixed alkyl/halo, in which some of the R groups are alkyl and some are halo, and R' is a hydrocarbyl group containing 1–20 carbon atoms. Examples of R' include methyl, ethyl, n-propyl, n-butyl, n-pentyl, isopentyl, n-hexyl, n-octyl, methylene cyclohexyl, benzyl, etc. Representative compounds include bis(diethylalumino)hexane, bis(dichloroalumino)hexane and bis(chloroethylalumino)hexane. These reagents can be readily prepared by a reaction of the dialkylaluminum hydride or dihaloaluminum hydride dialkyl etherate to an alkyne (e.g., hexyne). If the bis(halo(alkyl)alumino)alkane-type reagents are desired, they can be formed by a redistribution reaction of the bis(dihaloalumino)hexane with trialkyl aluminum (e.g., triethyl aluminum). Aromatic ketones or aromatic aliphatic ketones can be used. If desired, the aromatic ring or rings in the above-described classes of compound can be substituted with one or more alkyl groups. Some representative ketones which can be employed from these known classes of ketone include benzophenone, acetophenone, n-butylphenyl ketone, cyclohexylphenyl ketone, o-tolyl ethyl ketone, 9-fluorenone, and the like.

It has been found, in regard to the present invention that di(aromatic) ketones, such as benzophenone, reacted best with the di(halosubstituted alumino)alkanes and worst with the di(alkylsubstituted alumino)alkanes. For example, reaction with bis(diethylalumino)hexane gave only 9% of the desired product (1,1-diphenyl-1-heptene) as contrasted with 55% for bis(ethyl(chloro)alumino)hexane, and 71% for bis(dichloroalumino)hexane. The ethyl group-containing alumino hexanes gave reduction and ethylation products at 95% for the diethyl compound and 28% for the ethyl(chloro). The dichloro product gave 29% reduction of benzophenone but the desired hexylenation product was readily isolated by distillation.

Aliphatic aromatic ketones, e.g., acetophenone, are expected to yield a mixture of reduction, hexylenation and aldol condensation products. Use of bis(dichloroalumino)hexane with acetophenone gave 15%, 51% and 34%, of such products, respectively.

Wholly aliphatic ketones are deemed much less satisfactory in the instant process. For example, cyclohexanone was converted by bis(dichloroalumino)hexane into a 76:34 mixture of cyclohexanol and 2-cyclohexylidenecyclohexane. With bis(chloro(ethyl)alumino)hexane, cyclohexanone was almost completely ethylated (95%) and aldol condensation was minor.

In conducting the desired alkylenating reaction of the present invention the peferred ratio of bis(substituted alumino)substituted methane reagent to ketone can range from about 1.1:1 to about 2:1. Formation of a dietherate complex, such as shown in Example 2, by formation of the alkylenating reagents, in appropriate solvent (e.g., hydrocarbon or methylene chloride), in the presence of an ether (e.g., diethyl ether or tetrahydrofuran) is advantageous. In such cases, the molar ratios of ether to bis(substituted alumino)substituted methane reagent can range from about 1:1 to about 100:1, preferably about 2:1.

The following Examples further illustrate the present invention.

EXAMPLE 1

1,1-bis(diethylalumino)hexane was prepared by modification of a published procedure (G. Wilke et al. Justis Liebigs Ann. Chem., 1958, 618, 267). In anhydrous toluene at 0° C., pure 1-hexyne was treated with 1 molar equivalent of diethylaluminum hydride (Texas Alkyls, 98%). Then at room temperature a second equivalent of hydride was added and the reaction solution heated to 90° C. for 4 hours. The cooled solution was analyzed by hydrolysis of an aliquot: the collected $C_6$ hydrocarbon fraction was >98% composed of n-hexane.

EXAMPLE 2

1,1-bis(dichloroalumino)hexane was prepared from 1-hexyne and 2 molar equivalents of dichloroaluminum hydride (A. E. Finholt, J. Am. Chem. Soc., 1947, 69: 1199). Thus, a suspension of 3.84 grams (29 mmol) aluminum chloride in 20 milliliters of pentane and 50 milliliters of anhydrous diethyl ether was rapidly treated with 9.6 milliliters of 1.0 molar solution of lithium aluminum hydride in ether. After 60 minutes the ether was evaporated in vacuo and 25 milliliters of dry, deoxygenated toluene added to the residue. Finally, 1.5 grams (18 mmol) of 1-hexyne was slowly added to the toluene suspension. After 2 hours at 25° C. the reaction was heated for 45 minutes at 85° C. Insoluble salts were separated by filtration. The resulting solution was analyzed by hydrolysis: only n-hexane was found. Since the $Cl_2AlH$ was used as its etherate, the 1,1-bis(dichloroalumino)hexane was formed as its dietherate.

EXAMPLE 3

1,1-bis(chloro(ethyl)alumino)hexane was prepared by treating 1 molar equivalent of 1,1-bis(dichloroalumino)-hexane, (from Example 2), in toluene with 1 molar equivalent of neat triethylaluminum and heating the resulting mixture at 50° C. for 60 minutes.

COMPARATIVE EXAMPLE 4

A solution of 18 mmol of the compound from Example 1 in 10 milliliters of toluene was mixed with a solution of 5.0 grams (17.8 mmol) of benzophenone in 25 milliliters of anhydrous toluene. After 16 hours stirring at 25° C. the reaction mixture was slowly and cautiously hydrolyzed with gas evolution noted at 0° C. with 5 milliliters of 1N aqueous HCl. The separated organic layer was washed with aqueous $NaHCO_3$, dried over anhydrous $MgSO_4$ and evaporated. Gas chromatographic analysis and mass spectral identification of the components showed that the ketone had been consumed, but only traces of the desired 1,1-diphenyl-1-heptene had been formed. The principal outcome of the reaction was reduction: diphenylmethanol was separated and identified.

COMPARATIVE EXAMPLE 5

In another similar reaction to that of Comparative Example 4, using the reagent from Example 1, conducted for 17 hours at 25° C. and for 60 minutes at 110° C., a 9% yield of 1,1-diphenyl-1-heptene was obtained, but again reduction dominated. This finding suggests that the reduction to diphenylmethanol (as its aluminum salt) may be reversible.

EXAMPLE 6

In a reaction conducted in an analogous manner to Example 4, the reagent from Example 2 converted benzophenone into 1,1-diphenyl-1-heptene in a 71% yield. This product could easily be separated from reduction products by column chromatography on silica gel using hexane as the eluent, or even by simple distillation. This hydrocarbon was identified by spectral comparison with an authentic sample that was obtained by the partial reduction of known 1,1-diphenyl-1,6-heptadiene (J. J. Eisch et al., J. Am. Chem. Soc., 1979, 101: 1148).

EXAMPLE 7

In a similar manner to Example 4, after 16 hours at 25° C., 1,1-bis(chloro(ethyl)alumino)hexane (from Example 3) converted benzophenone into 1,1-diphenyl-1-heptene in 55% yield.

We claim:

1. A process for the alkylenation of the carbonyl oxygen atom of a ketone which comprises reacting the ketone with a bis(substituted alumino)substituted methane to form the corresponding olefin.

2. A process as claimed in claim 1 wherein the bis(substituted alumino)methane has the formula:

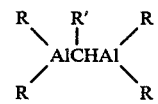

where R is alkyl, halo or mixed alkyl/halo and R' is $C_1$–$C_{20}$ hydrocarbyl.

3. A process as claimed in claim 2 where R' is pentyl.

4. A process as claimed in claim 1 wherein bis(dichloroalumino)hexane is used.

5. A process as claimed in claim 1 wherein bis(diethylalumino)hexane is used.

6. A process as claimed in claim 1 wherein bis(dichloro(ethyl)alumino)hexane is used.

7. A process as claimed in claim 1 wherein the ketone is an aromatic group-containing ketone.

* * * * *